United States Patent
Goebel et al.

(10) Patent No.: US 12,042,130 B2
(45) Date of Patent: Jul. 23, 2024

(54) LIGHT SOURCE AND SYSTEM FOR AND METHOD OF FLUORESCENCE DIAGNOSIS

(71) Applicant: KARL STORZ SE & CO. KG, Tuttlingen (DE)

(72) Inventors: Werner Goebel, Tuttlingen (DE); Henrik Spath, Tuttlingen (DE); Franz Bauer, Tuttlingen (DE); Costantino Pascale, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 657 days.

(21) Appl. No.: 16/885,410

(22) Filed: May 28, 2020

(65) Prior Publication Data
US 2020/0383558 A1    Dec. 10, 2020

(30) Foreign Application Priority Data
Jun. 6, 2019 (DE) ..................... 10 2019 115 276.3

(51) Int. Cl.
*A61B 1/04* (2006.01)
*A61B 1/045* (2006.01)
(Continued)

(52) U.S. Cl.
CPC .............. *A61B 1/043* (2013.01); *A61B 1/045* (2013.01); *A61B 1/0646* (2013.01);
(Continued)

(58) Field of Classification Search
CPC ..... A61B 1/0638; A61B 1/043; A61B 5/0071; A61B 1/0646; A61B 5/0075;
(Continued)

(56) References Cited

U.S. PATENT DOCUMENTS

| 5,507,287 A | 4/1996 | Palcic et al. |
| 6,899,675 B2 | 5/2005 | Cline et al. |

(Continued)

FOREIGN PATENT DOCUMENTS

| CN | 204379226 U | 6/2015 |
| DE | 10252313 A1 | 6/2004 |

(Continued)

OTHER PUBLICATIONS

European Search Report for corresponding European Application No. 20175771.3, mailed Oct. 9, 2020.
(Continued)

*Primary Examiner* — Rebecca A Volentine
(74) *Attorney, Agent, or Firm* — Jason H. Vick; Sheridan Ross, PC (57) ABSTRACT

A light source configured for fluorescence diagnosis comprises a first semiconductor-illuminant based light emission unit configured to emit first light in a broadband first wavelength spectrum, a second semiconductor-illuminant based light emission unit configured to emit second light in a narrowband second wavelength spectrum for excitation of fluorescence, a spectral filter for the first light emission unit that is configured to block spectral components of the first wavelength spectrum which are assigned to a color channel of a camera the fluorescence is to be detected with, and to transmit remaining spectral components of the first wavelength spectrum, a brightness control for the first light emission unit configured to dim the intensity of the emitted first light, and an optical intensity attenuator for the first light emission unit that is configured to reduce the intensity of the emitted first light below the minimum intensity obtainable through the brightness control without the intensity attenuator.

19 Claims, 2 Drawing Sheets

(51) Int. Cl.
  *A61B 1/06* (2006.01)
  *A61B 5/00* (2006.01)
  *G02B 5/20* (2006.01)
  *H05B 45/10* (2020.01)

(52) U.S. Cl.
  CPC .......... *A61B 1/0684* (2013.01); *A61B 5/0071* (2013.01); *G02B 5/205* (2013.01); *H05B 45/10* (2020.01)

(58) Field of Classification Search
  CPC .......... A61B 1/00186; A61B 1/000094; A61B 1/063; A61B 1/0669; A61B 1/0653; A61B 1/00009; G01N 21/6456; G02B 21/16; G01J 3/10; G01J 3/4406
  See application file for complete search history.

(56) References Cited

U.S. PATENT DOCUMENTS

| | | | |
|---|---|---|---|
| 7,704,206 B2 | 4/2010 | Suzuki et al. |
| 8,167,794 B2 | 5/2012 | Matsumoto et al. |
| 8,547,427 B2 | 10/2013 | Hanano et al. |
| 8,616,747 B2 | 12/2013 | Yabe |
| 8,998,468 B2 | 4/2015 | Jaffe et al. |
| 9,025,244 B2 | 5/2015 | Reimer et al. |
| 9,186,054 B2 | 11/2015 | Godo et al. |
| 10,690,904 B2 | 6/2020 | Otterstrom et al. |
| 2004/0152987 A1 | 8/2004 | Haisch |
| 2007/0093691 A1 | 4/2007 | Kobayashi |
| 2012/0057226 A1 | 3/2012 | Kuster |
| 2013/0242595 A1* | 9/2013 | Jaffe ................ G02B 6/0003 362/552 |
| 2014/0054450 A1 | 2/2014 | Shirota et al. |
| 2015/0105668 A1* | 4/2015 | Ehrhardt ............ G01N 21/6456 600/476 |
| 2016/0022126 A1 | 1/2016 | Ramesh et al. |
| 2016/0062103 A1 | 3/2016 | Yang et al. |
| 2017/0235118 A1 | 8/2017 | Kuster et al. |
| 2018/0364470 A1 | 12/2018 | Hauger et al. |

FOREIGN PATENT DOCUMENTS

| | | |
|---|---|---|
| DE | 102006049856 A1 | 4/2007 |
| DE | 102010044503 A1 | 3/2012 |
| DE | 102013111368 A1 | 4/2015 |
| DE | 102017210274 A1 | 12/2018 |
| EP | 1301118 B1 | 9/2006 |
| EP | 1258220 B1 | 8/2008 |
| EP | 1759628 B1 | 10/2010 |
| EP | 2301417 B1 | 2/2013 |
| EP | 2122331 B1 | 7/2017 |
| EP | 3205257 A1 | 8/2017 |
| EP | 3257432 A1 | 12/2017 |
| JP | 5518686 B2 | 6/2014 |

OTHER PUBLICATIONS

Notification of First Office Action (Including Translation) for corresponding Chinese Patent Application No. 202010504214.8, mailed Jul. 29, 2023.

* cited by examiner

LIGHT SOURCE AND SYSTEM FOR AND METHOD OF FLUORESCENCE DIAGNOSIS

CROSS REFERENCE TO RELATED APPLICATIONS

This application claims priority from German patent application No. 10 2019 115 276.3, filed on Jun. 6, 2019. The entire content of this priority application is incorporated herein by reference.

FIELD OF THE INVENTION

The invention relates to a light source for fluorescence diagnosis, a system for fluorescence diagnosis that comprises such a light source, and a method of fluorescence diagnosis.

BACKGROUND

Fluorescence diagnosis is used in medicine for assessment of the state of biological tissue, for example generally for tissue differentiation, in particular for tumor identification, but also for identification of blood circulation and vitality. However, fluorescence diagnosis can also be used for technical diagnosis purposes in industrial or scientific applications. Without limiting the generality, the invention will be described on the basis of medical fluorescence diagnosis.

In the medical field, fluorescence diagnosis has developed to a very promising alternative or supplement in the identification and treatment of e.g. neoplastic changes. The fluorescence diagnosis is based on the interaction of light of a suitable wavelength with a fluorescent substance present in the tissue area to be examined. A fluorescent substance may be a fluorescent dye which has been introduced before-hand into the tissue area to be examined, for example by administering the fluorescent substance itself or a pre-cursor thereof to the patient to be examined. A fluorescent substance however can also be a substance which is already present in the target area, for example a tissue specific substance which is excited to auto-fluorescence by light in a suitable spectral range. The present invention can encompass both cases.

In fluorescence diagnosis, typically not only fluorescence is detected, but in addition to the fluorescence observation, the background, e.g. areas in the image of the observation area without fluorescence, is illuminated to enable the user of the system, typically a physician, to better orient him- or herself in the observation area, in order to improve the tissue differentiation.

Conventional fluorescence diagnosis systems comprise a light source having a Xenon lamp. With such Xenon-lamp based systems, a residual transmission of the excitation light is admitted, for example from an overlapping region of the excitation filter installed in the light source with the observation filter or by means of an increased transmission within the detection region of the observation filter. It is necessary in this context that the detected background light is detected in a camera channel separated from the fluorescence signal. For example, if the fluorescence is in the near-infrared spectral range and is detected in the blue-channel of the camera, the light for the background illumination is to be provided in the green-red spectral range in order to ensure an unambiguous discrimination between fluorescence and background.

Xenon-lamp based light sources have the disadvantage of a relative short lifetime. The disadvantage of such conventional fluorescence diagnosis systems consists in additional costs due to a replacement of the Xenon lamp on the one hand, and in downtimes due to maintenance or replacement, on the other hand.

Meanwhile, light sources for fluorescence diagnosis are known, for example from DE 10 2013 111 368 A1, which comprise semiconductor-illuminants, such as light emitting diodes, laser diodes, superluminescence diodes and the like. Also in case of semiconductor-illuminant based light sources for fluorescence diagnosis, the illumination modes for white-light observation and fluorescence excitation should be provided as in case of the conventional Xenon-lamp based light sources, wherein again an illumination of the image background, i.e. of the image areas without fluorescence, is desired in the fluorescence mode in order to enable the user the detection of e.g. certain anatomic structures for better orientation.

Semiconductor-illuminant based light sources for the fluorescence diagnosis comprise, for example, a broadband emitting light emitting diode, in particular a white-light emitting diode, as well as a further, narrowband emitting light emitting diode, wherein the latter emits in the spectral range of the absorption of the fluorescent dye. By this approach, a fast, optionally camera-synchronous, switching between white light and fluorescence excitation light as well as the simultaneous white-light/fluorescence illumination (in the latter case for two-chip-cameras) is made possible. For a continuous working in the fluorescence mode, however, a background illumination also is advantageous as with the conventional Xenon lamp-based light sources. In case of a phosphor-converted white-light light emitting diode for example, the additional switching-on of this light emitting diode would however cover the entire visible spectral range and, thereby, all camera channels (red-green-blue), i.e. also the camera channel which detects the fluorescence. Therefore, the background illumination has to be provided within the spectral range of that camera channel which detects no fluorescence signal.

SUMMARY

It is an object of the invention to provide a light source for fluorescence diagnosis which is based on semiconductor-illuminants, and which enables a background illumination for improved orientation in the observation area without outshining the fluorescence in the fluorescence mode.

It is a further object of the invention to provide an improved system for fluorescence diagnosis.

It is a further object of the invention to provide an improved method of fluorescence diagnosis.

According to an aspect, a light source for fluorescence diagnosis is provided, the light source providing an illumination beam path and comprising a first semiconductor-illuminant based light emission unit configured to emit first light in a broadband first wavelength spectrum, and a second semiconductor-illuminant based light emission unit configured to emit second light in a narrowband second wavelength spectrum for excitation of fluorescence, further comprising a spectral filter for the first light emission unit that is configured to block spectral components of the first wavelength spectrum which are assigned to a color channel of a camera the fluorescence is to be detected with, and to transmit remaining spectral components of the first wavelength spectrum, further comprising a brightness control for the first light emission unit for dimming the intensity of the emitted first light, and an optical intensity attenuator for the first light emission unit that is configured to reduce the intensity of the emitted first light below the minimum intensity obtainable through the brightness control without the intensity attenuator.

The first semiconductor-illuminant based light emission unit emits light in a broadband first wavelength spectrum, which is transmitted into the observation area, preferably without changes, for a white light observation of the observation area, and which is changed spectrally and as to its intensity in a certain manner in the fluorescence observation mode (briefly fluorescence mode), in order to provide a suitable background illumination. To spectrally change the first light emitted from the first light emission unit for providing a background illumination of the illumination area, the light source comprises a spectral filter which can be introduced into the illumination beam path of the first light emission unit in the fluorescence mode. This spectral filter is adapted with respect to the spectral transmission characteristics such that spectral components of the first light that are assigned to that camera channel the fluorescence is to be detected with, are blocked, and simultaneously the remaining spectral components of the first light that correspond to the spectral ranges of the remaining camera channels, are transmitted. However, according to the present disclosure, not only a spectral change of the light emitted from the first light emission unit is provided, but also a change of the intensity of the light emitted from the first light emission unit for the purpose of background illumination. To this end, a brightness control is provided for the first light emission unit, through which the intensity of the first light emitted from the first light emission unit can be dimmed. The brightness control is adapted to control the intensity of the first light continuously between two intensity values, for example a maximum and a minimum intensity. The brightness control can be configured as an electrical or electronic dimming circuit controlling the driving current of the first light emission unit. In other configurations, the brightness control can comprise a continuously dimming disc which is motor-driven.

Light of very weak intensity is required for the background illumination in order to avoid an outshining of the typically weak fluorescence signals. If the brightness control is configured as an electrical dimming circuit for example, dimming by means of the brightness control may not be sufficient for the required reduction of the intensity of the background illumination, because semiconductor-illuminants such as e.g. light emitting diodes require a minimum current for reliable operation. This means that the driving current of the light emitting diode cannot be minimized to an arbitrary value, but only down to a certain threshold. Once the driving current falls below this threshold, no continuous light emission of the light emitting diode occurs. Above this minimum current threshold, light emitting diodes provide dimmed light, however the intensity of that light is still significantly above the values required for background illumination. Therefore, the light source according to the present disclosure further comprises an optical intensity attenuator for the first light emission unit with which the intensity of the emitted first light can be reduced below the minimum intensity obtainable or reachable through the brightness control without the intensity attenuator.

The optical intensity attenuator may comprise one or more mechanical grids or gratings, or in other configurations one or more neutral density filters. A neutral density filter reduces the intensity of light over a broad band by a certain factor, which typically is 10 to 1000 times. The intensity attenuator is used, in the fluorescence mode of the light source, simultaneously with the spectral filter in the illumination beam path of the first light emission unit. Thus, a spectral and also an intensity adaptation of the light emitted from the first light emission unit are simultaneously performed for background illumination.

A further advantage of the combination of brightness control and optical intensity attenuator is that an adjustment of the intensity of the background illumination via the brightness control is possible over a continuous range of intensity values, which in turn is not possible by only using an optical intensity attenuator, for example a neutral density filter with fixed neutral densities. The neutral density filter provides a strong reduction of the intensity by for example, more than 90%, and the brightness control in addition enables the user to perform a fine adjustment (increase or decrease) or a continuously variable adjustment of the brightness of the background illumination as it is best suitable for the user and/or the respective application (for example dependent on the special diagnostic field). In case of a brightness control of the type of a dimming circuit with which the driving current of the semiconductor-illuminant based light emission unit can be reduced as far as possible, a further advantage is that lost power and heat emission of the light emission unit can be minimized.

In order to be able to use the light source for a white-light mode as well as for a fluorescence mode, the spectral filter and the intensity attenuator preferably are movable in order to be introducible in or removable from the illumination beam path of the first light emission unit.

Introducing and removing of the spectral filter and of the intensity attenuator is preferably realized in an automated manner, and, for example, occurs automatically through a control unit or control circuit upon switching the light source between white-light mode and fluorescence mode.

The spectral filter and the intensity attenuator may be movable in translational or rotational fashion.

Preferably, the spectral filter and the intensity attenuator are arranged one behind the other in direction of the illumination beam path on a joint carrier, wherein the carrier comprises an actuator.

In this configuration, a particularly compact configuration of the light source is provided, by the intensity attenuator and the spectral filter forming an optical unit. The mentioned actuator of the filter carrier can be connected to a control circuit which actuates the actuator upon switching of the light source between white-light mode and fluorescence mode, in order to remove the spectral filter and the intensity attenuator in the white-light mode from the illumination beam path of the first light emission unit, and to introduce them into same in the fluorescent mode.

The first light emission unit preferably comprises a white-light light emitting diode. The white-light light emitting diode may be a luminophore-converted, in particular phosphor-converted white-light light emitting diode. The first light emitted by the first light emission unit thus comprises a wavelength spectrum which may include the entire visible spectrum.

The second light emission unit may comprise a light emitting diode which emits in a narrow band, or a laser diode. The narrowband light emitting diode or the laser diode preferably are adapted to the absorption spectrum of the used fluorescence marker. For example, if ICG (indocyanine green) is used as the fluorescent dye, the second light emission unit may be a light emitting diode emitting in a narrow band or a laser diode with an emission peak at about 785 nm. For the purpose of auto-fluorescence diagnosis, the second light emission unit may comprise a light emitting diode comprising an emission peak at about 405 nm.

Preferably, the brightness control is configured to reduce the intensity of the first light emitted from the first light emission unit to a value in a range from 2% to 15%, preferably from 5% to 10% of the (maximum) output intensity of the first light emission unit. The optical intensity attenuator, in turn, which for example comprises one or more neutral density filters, is preferably configured to further reduce the light emission already reduced through the brightness control, e.g. by a factor of 10 to 1000, preferably by a factor of 100 (this corresponds to a density 2 for a neutral density filter). It is an aim to adapt the intensity of the background illumination approximately to the intensity of the detected fluorescence signals so that both, background illumination and fluorescence signals, generate approximately similar intensity values on the respective camera sensors (chips)/camera channels.

A light intensity of the background illumination which is strongly reduced in this way and adapted to the intensity of the fluorescence signals is particularly well suited for the orientation of the user in the observation area. Such a reduction of the intensity of the first light emitted from the first light emission unit may not be obtainable by only dimming a light emitting diode. Therefore, the combination of brightness control and intensity attenuator, for example neutral density filter, is particularly advantageous.

When the optical intensity attenuator comprises a neutral density filter, the neutral density filter preferably comprises a neutral density in a range from 1 to 4, preferably in a range from 1.5 to 3, further preferably a neutral density of 2.

A neutral density filter having a neutral density of 1 has a transmissivity of 10%, i.e. one tenth of the original amount of light incident onto the filter is transmitted by the filter. A neutral density of 2 means a transmissivity of 1%, a neutral density of 3 a transmissivity of 0.1%, and a neutral density of 4 a transmissivity of 0.01%. A neutral density of 2 is particularly advantageous in combination with an electrical brightness control.

The spectral filter may be a long pass filter, a band reflection filter or a short pass filter. A long pass filter is suitable when the fluorescence is detected in the blue channel, a band reflection filter is suitable when the fluorescence is detected in the green channel, and a short pass filter is suitable when the fluorescence is detected in the red channel of the camera.

According to a further aspect, a system for fluorescence diagnosis is provided, comprising a light source according to one or more of the above indicated configurations, and a camera comprising a first color channel for detection of fluorescence in an observation area and further color channels for picking up images for tissue differentiation in the observation area.

The system for fluorescence diagnosis according to the present disclosure has the same advantages and configurations as indicated in the dependent claims for the light source.

Preferably, the system comprises a control unit for switching the light source between a white-light mode and a fluorescence mode, wherein the control unit is configured, in the fluorescence mode, to reduce the intensity of the first light emitted from the first light emission unit through the brightness control and to introduce the spectral filter and the neutral density filter into the illumination beam path.

By this measure, an automatic control of the light source is provided, wherein the control also includes an automated movement of the spectral filter and of the neutral density filter into and out of the illumination beam path. The actuation of the control unit may be realized, for example, through a foot switch or through a switch on the camera head.

The camera may be a one-chip-, two-chip or three-chip-camera.

According to a further aspect, a method of fluorescence diagnosis is provided, comprising the steps:
  emitting first light in a broadband first wavelength spectrum from a first semiconductor-illuminant based light emission unit,
  emitting second light in a narrowband second wavelength spectrum from a second semiconductor-illuminant based light emission unit for excitation of a fluorescence in an observation area,
  detecting the fluorescence in a first color channel of a camera,
  blocking spectral components of the first wavelength spectrum through a spectral filter, which spectral components are assigned to the first color channel of the camera, and transmitting the remaining spectral components of the first wavelength spectrum into the observation area for providing a background illumination,
  wherein providing the background illumination further comprises:
    dimming the intensity of the emitted first light through a brightness control for the first light emission unit,
    further reducing the intensity of the emitted first light below the minimum intensity obtainable through the brightness control, through an optical intensity attenuator,
  picking up background images of the observation area in other color channels of the camera than the first color channel, based on the background illumination.

The indicated steps of the method may be carried out in the indicated order, but also in other orders, and a plurality of the indicated steps may be carried out simultaneously.

The method according to the present disclosure has the same or similar advantages as the light source according to the present disclosure.

Preferably, the background illumination is provided with an intensity in the observation area which amounts to from 0.01% to 0.2%, preferably from 0.05% to 0.1% of the maximum output intensity of the first light emission unit.

For a white-light observation of the observation area, preferably the entire first wavelength spectrum of the first light, preferably without intensity reduction, is transmitted into the observation area.

Further advantages and features are apparent from the following description of the accompanying drawings.

It is to be understood that the features indicated above and those to be explained below are not only usable in the respectively indicated combination, but also in other combinations or in isolation without departing from the scope of the present invention.

BRIEF DESCRIPTION OF THE DRAWINGS

Embodiments of the invention are shown in the drawings and will be described with reference thereto in more detail below. In the drawings.

DETAILED DESCRIPTION OF EXEMPLARY EMBODIMENTS

Figure 1:
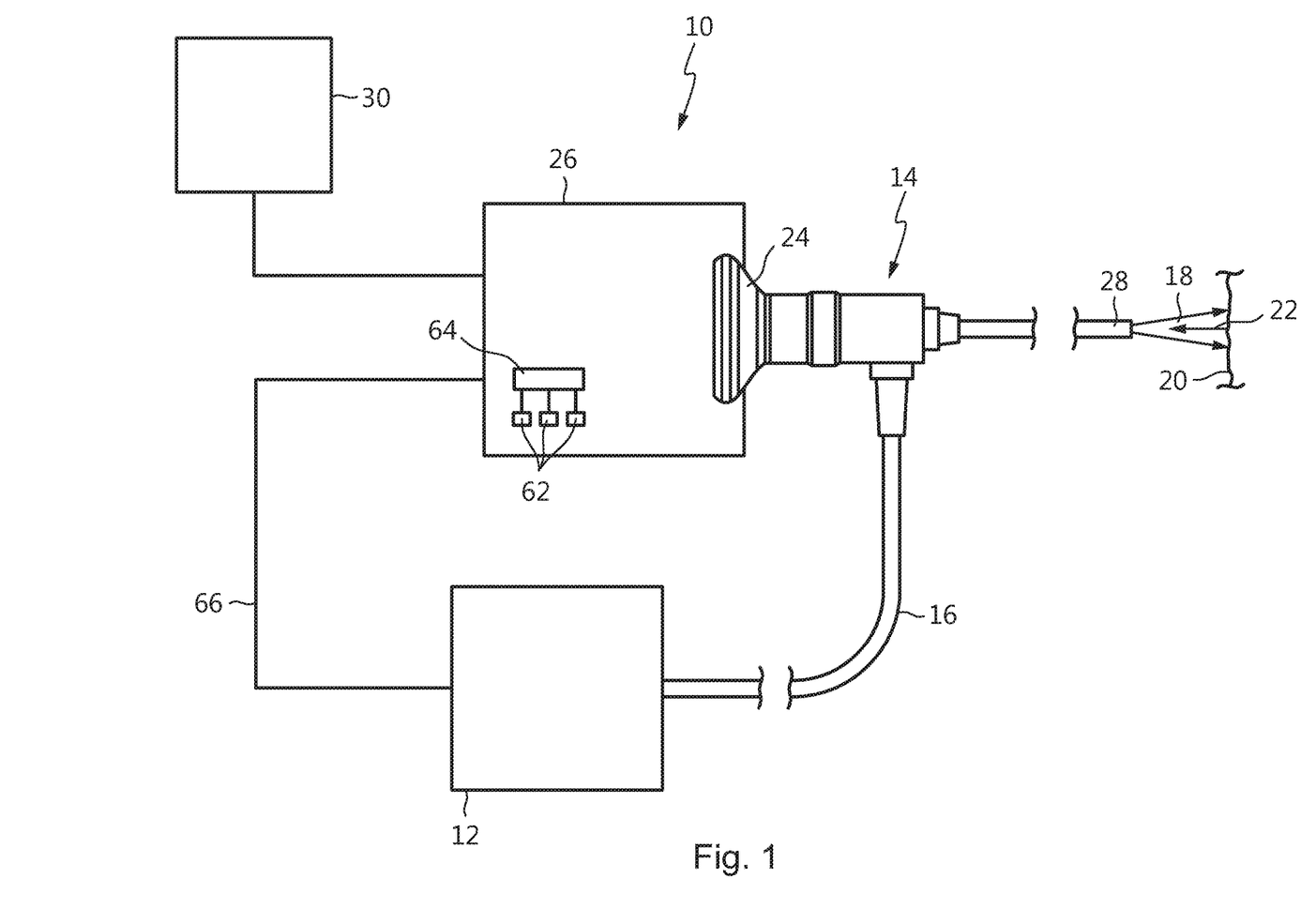
FIG. 1 shows an embodiment of a system for fluorescence diagnosis in a block diagram.

FIG. 1 shows a system for fluorescence diagnosis labeled with the general reference numeral 10. In the embodiment shown, the system 10 is an endoscopic fluorescence diagnosis system.

The system 10 comprises a light source 12 which emits, in a fluorescence mode, light in a narrowband wavelength spectrum for excitation of a fluorescence, as will be described below. The light source 12 is further configured to emit light in a broadband wavelength spectrum. In a white-light mode, the light source 12 emits light comprising the full broadband wavelength spectrum. The broadband wavelength spectrum preferably includes the entire visible spectrum. In the fluorescence mode, the light source 12 emits, in addition to the narrowband wavelength spectrum for excitation of the fluorescence, light for a background illumination of the observation area in which the fluorescence is excited. For the background illumination, the light with the broadband wavelength spectrum is spectrally restricted and the intensity of the light is strongly attenuated, as will be described later.

The system 10 comprises an endoscope 14 which is connected to the light source 12 via a light wave guide in form of a light guide cable 16. Light emitted from the light source 12 is fed into the endoscope 14 via the light guide cable 16, and is directed from the endoscope onto an observation area 20, for example a tissue area in the human or animal body, as illustrated with a light cone 18.

The light in the narrowband wavelength spectrum which is emitted from the light source 12 serves for excitation of fluorescence in the observation area 20. To this end, a fluorescent dye may be concentrated in the observation area 20. The narrowband wavelength spectrum emitted from the light source 12 is the spectral range of the fluorescence excitation of the fluorescent dye. The fluorescent dye may be, for example, ICG (indocyanine green) having an absorption peak at about 785 nm.

The system 10 however can also be used for auto-fluorescence diagnosis. In this case, no additional fluorescent dye is introduced into the body, but the body's own substances are excited to fluorescence by the narrowband excitation light emitted from the light source 12. Therefore, the term fluorescence also encompasses auto-fluorescence in the present disclosure.

The fluorescence excited in the observation area 20, as indicated with an arrow 22, is received by the endoscope 14 and guided through the optical system (not shown) of the endoscope 14, which may be formed by lenses or a fiber optics, to an eyepiece 24 to which a camera 26 is connected. The camera 26 can comprise a single image pick-up chip, or two or three image pick-up chips. Light of the background illumination scattered back from the observation area is also received by the endoscope 14 and guided through the optical system of the endoscope 14 to the camera 26.

It is to be understood that the camera 26 can also be integrated into the endoscope 14. Nowadays, miniaturized cameras are available which even may be integrated into the tip 28 of the endoscope 14.

It is further to be understood that the system 10 can comprise a microscope or an exoscope instead of the endoscope 14.

The camera 26 is connected to a monitor 30 on which the camera image may be visually represented.

Figure 2:
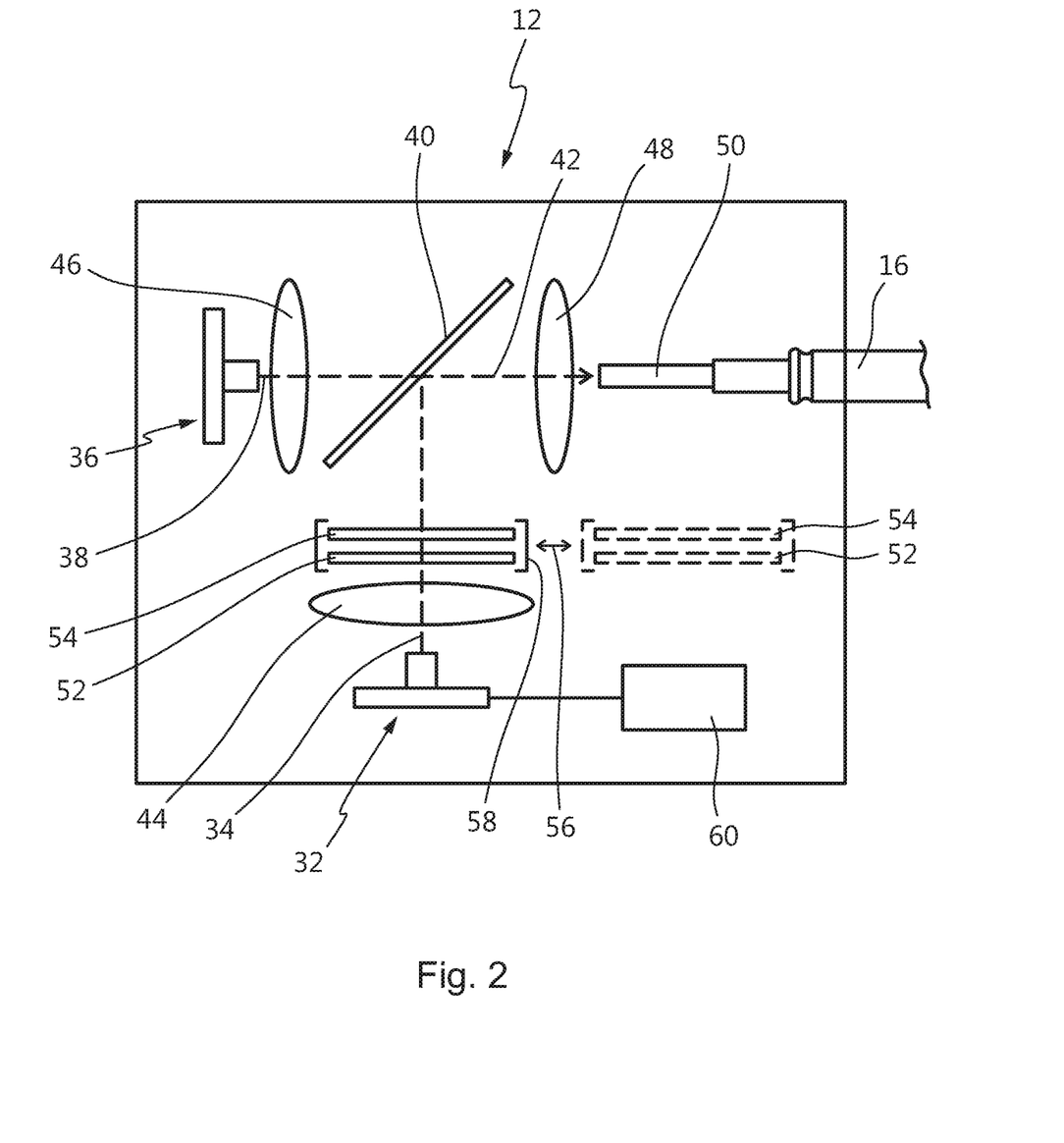
FIG. 2 shows an embodiment of a light source of the system in FIG. 1.

With reference to FIG. 2, the light source 12 will be described in more detail in the following.

The light source 12 provides an illumination beam path. The light source 12 comprises a first semiconductor-illuminant based light emission unit 32. The light emission unit 32 is configured to emit first light 34 (reference numeral 34 will also be used for the illumination beam path of the first light emission unit 32 in the following), indicated by a broken line, in a broadband first wavelength spectrum. In particular, the light emission unit 32 is configured to emit white light. The light emission unit 32 may be a white-light light emitting diode (white light-LED), for example. The white-light LED may be, in particular, a phosphor-converted white-light LED. Phosphor is typically used as a luminophore for a blue LED in order to generate white light. Instead of phosphor, the LED may comprise any other luminophore suitable to generate white light.

The light source 12 comprises a second semiconductor-illuminant-based light emission unit 36 configured to emit second light 38 (reference numeral 38 will be also used for the illumination beam path of the second light emission unit 36 in the following) indicated by a broken line, in a narrowband second wavelength spectrum for excitation of fluorescence. The second light emission unit 36 may be a narrowband-emitting light emitting diode, which emits in the blue, green, red, near-infrared or infrared wavelength spectrum, dependent on the fluorescent dye to be excited to fluorescence. The second light emission unit 36 may, for example, comprise a light emitting diode, the emission peak of which is at about 785 nm so that for example the fluorescence of ICG may be excited with such a light emitting diode. In case of the excitation of auto-fluorescence, the second light emission unit 36 may comprise a light emitting diode which emits light in a narrow band with an emission peak about 405 nm. Instead of a light emitting diode, the second light emission unit 36 may also comprise a laser diode, which emits in a narrow band in the near-infrared spectral range or in the infrared spectral range, for example.

The light source 12 further comprises a beam combiner (or beam splitter) 40, which combines the light 34 emitted from the first light emission unit 32 and the light 38 emitted from the second light emission unit 36 to a joint illumination beam path 42. The beam combiner 40 can also be configured as a dichroic mirror.

Optics 40 may be assigned to the first light emission unit 32 which collimates the light emitted form the light emission unit 32. Also, optics 46 may be assigned to the second light emission unit 36 which collimates the light emitted from the light emission unit 36. Further optics 48 may be arranged downstream of the beam combiner 40 in order to bundle the light emitted from the light emission unit 32 and/or the light emission unit 36 in order to couple the light with losses as least as possible into a fiber bundle 50 of the light guide cable 16. The optics 44, 46 and 48 may also be aspherized.

A spectral filter 52 and an optical intensity attenuator 54 are assigned to the first light emission unit 32. The spectral filter 52 and the optical intensity attenuator 54, which are configured as an optical unit, are used together for the background illumination of the observation area 20 in the fluorescence mode of the system 10 or the light source 12. Contrary to the order of the spectral filter 52 and of the intensity attenuator 54 shown in FIG. 2, the order may also be reversed. The intensity attenuator 54 comprises one or more neutral density filters in the present embodiment.

The spectral filter 52 is configured to block spectral components of the wavelength spectrum of the first light 34, which spectral components are assigned to the color channel of the camera 26 the fluorescence is to be detected with, and to transmit remaining spectral components of the broadband wavelength spectrum of the first light 34. For example, when the fluorescence is detected in the blue channel of the camera 26, the spectral filter 52 is configured to block the blue spectral components in the broadband wavelength spectrum of the first light 34, and to transmit the red and green spectral components of the light 34 for background illumination. In this example, the spectral filter 52 may be configured as long pass filter. When, in another example, the fluorescence is detected in the red channel of the camera 26, the spectral filter 52 is configured to block the red spectral components of the light 34, and to transmit the green and blue spectral components of the light 34. In this case, the spectral filter 52 may be configured as a short pass filter. When, in a further example, the fluorescence is detected in the green channel of the camera 26, the spectral filter 52 may be configured as a band rejection filter, so that it blocks the green spectral components of the broadband wavelength spectrum of the first light 34 and transmits the red and blue spectral components of the light 34.

The spectral filter 52 thus serves for the spectral narrowing of the broadband wavelength spectrum of the first light 34 for the background illumination in the fluorescence mode.

The neutral density filter 54 serves to strongly reduce the intensity of the light 34 emitted from the light emission unit 32 such that the background illumination does not outshine the fluorescence in the image of the camera 26. The neutral density filter 54, which may also be referred to as a grey filter, attenuates the intensity of the light 34 in a broadband manner. The neutral density filter 54 may have a neutral density in a range from 1 to 4, preferably in a range from 1.5 to 3, further preferably a neutral density of 2. A neutral density of 1 means that the neutral density filter 54 transmits 10% of the light incident on the neutral density filter 54. A neutral density of 2 means that the neutral density filter 54 transmits 1% of the light 34 incident thereon. A neutral density of 3 means a transmissivity of 0.1%, and a neutral density of 4 means a transmissivity of the neutral density filter 54 of 0.01%.

The spectral filter 52 and the neutral density filter 54 are both movable in order to be introducible into and to be removable from the illumination beam path 34 of the first light emission unit 32, as indicated by a double arrow 56 in FIG. 2. The spectral filter 52 and the neutral density filter 54 are shown in their positions removed from the illumination beam path 34 of the first light emission unit 32 by broken lines in FIG. 2.

The neutral density filter 54 and the spectral filter 52 may be arranged one behind the other in direction of the illumination beam path 34 of the light emission unit 32 on a joint filter carrier 58, which comprises an actuator (not shown), in order to move the filter carrier 58 according to a double arrow 56. Instead, as shown in FIG. 2, of a translatory movability of the carrier 58 and thus the filters 52 and 54, the filters may also be arranged on a rotatable filter wheel which can be rotated or pivoted about a rotation axis, in order to move the filters 52, 54 into and out of the illumination beam path 34 of the first light emission unit 32.

The light source 12 further comprises, in addition to the neutral density filter 54, a brightness control 60 for the first light emission unit 32. Here, the brightness control 60 is configured as electrical or electronic brightness control which comprises a dimming circuit with which the driving current for the light emission unit 32 may be reduced in order to dim the intensity of the emitted first light 34. The combination of the brightness control 60 and the neutral density filter 54 is particularly advantageous. Semiconductor-illuminants as used for the first light emission unit 32 can be dimmed, however they require always a minimum driving current, i.e. a driving current above a certain threshold. In case the driving current falls below the threshold, the semiconductor-illuminant goes out. With a brightness control or dimming circuit 60, the intensity of the first light 34 thus can only be reduced to a minimum which still is significantly too high for a suitable background illumination in the observation area 20. The neutral density filter 54 now enables to reduce the intensity of the light 34 emitted from the light emission unit 32 below the minimum intensity that can be obtained through the brightness control or dimming circuit 60 without the neutral density filter 54. On the other hand, the electric brightness control or dimming circuit 60 allows for a continuous fine adjustment of the intensity of the background illumination in the observation area 20. Through the brightness control 60, the intensity may be varied, for example, in a range of a few±%. For example, when the background illumination for tissue differentiation is too low, the intensity may be increased by increasing the driving current by means of the electric brightness control 60, until the desired intensity of the background illumination is reached. In the same way, by decreasing the driving current by means of the brightness control 60, the intensity may be reduced provided that the driving current does not fall below the threshold for light emission. Therefore, the neutral density filter 54 may be adapted such that it provides an intensity basis value for the background illumination for a medium driving current for the light emission unit 32, and the intensity basis value then can be finely adjusted up or down via the brightness control 60.

The brightness control 60 is configured to reduce the intensity of the first light emitted from the first light emission unit 32 to a value in a range from 2% to 15%, preferably from 5% to 10% of the (maximum) output intensity of the first light emission unit. The neutral density filter 54 in turn is configured to further reduce the light emission already reduced through the brightness control 60, e.g. by a factor of 10 to 1000, preferably by a factor of 100 (corresponding to a density 2 of a neutral density filter).

The camera 26 may comprise an image pick-up chip having three color channels RGB (red-green-blue), and optionally a further channel W (white). However, the camera 26 can also comprise two image pick-up chips, which comprise one, three or four color channels in each case. The camera 26 can also comprise three image pick-up chips which selectively detect one color channel (red-green-blue) in each case.

Different operating modes are possible for the system 10, in order to switch the system 10 into the white-light mode and into the fluorescence mode. The switching between the different operation modes may be realized via switches 62, for example on the head of the camera 26. A control unit 64, which is shown here exemplarily on the head the camera 26, but which also may be integrated into the light source 12, is connected to the light source 12 via a signal line 66. The control unit 64 switches the light source 12 between the white-light mode and the fluorescence mode, depending on the selected operating mode. The white-light mode and the fluorescence mode may be individually switched on and off, for example. It is also possible to realize a switching between the white-light mode and the fluorescence mode by shuttering, e.g. synchronous with the camera with a frequency of 50 to 60 Hz. Both light emission units 32 and 36 can also be operated simultaneously, wherein in this case the camera 26 should be a two-chip-camera 26.

In the white-light mode, the light source 12 is driven such that only the first light emission unit 32 emits light, namely white light, wherein the white light is transmitted into the observation area 20 without spectral narrowing. In this instance, the spectral filter 52 and the neutral density filter 54 are not positioned in the illumination beam path of the light emission unit 32, but they are displaced out of the illumination beam path (broken lines in FIG. 2). Further, in the white-light mode, the electrical brightness control 60 may supply maximum driving current to the light emission unit 32 for a particularly bright white-light illumination of the observation area 20.

Upon switching from the white-light mode into the fluorescence mode, the control unit 64 is configured to reduce the intensity of the first light 34 emitted from the first light emission unit 32 by means of the electrical brightness control (dimming circuit) 60, and to introduce the spectral filter 52 and the neutral density filter 54 into the illumination beam path of the first light 34. Simultaneously, the control unit 64 activates the second light emission unit 36, which emits the fluorescence excitation light. By means of the background illumination provided by the first light emission unit 32, the fluorescence in the observation area 20 can then be observed on the monitor 30 with improved orientation of the observer. The first light emission unit 32 thus serves for the white-light observation in the white light mode, wherein the light 34 emitted from the light emission unit 32 is then neither spectrally narrowed nor intensity-reduced, and, in the fluorescence mode, the first light emission unit 32 serves to provide background illumination, which is spectrally narrowed and strongly intensity-reduced.

A method of fluorescence diagnosis may be carried out as follows. The first light 34 is emitted from the light emission unit 32 with a broadband first wavelength spectrum. Simultaneously, the second light 38 is emitted from the second light emission unit 36 in a narrowband second wavelength spectrum. The fluorescence excited by the light emitted from the second light emission unit 36 is detected or observed in the observation area 20 by means of the camera 26. Spectral components of the wavelength spectrum emitted from first light emission unit 32 which are assigned to the color channel of the camera 26, the fluorescence is to be detected with, are blocked by the spectral filter 52, and the remaining spectral components of the first light 34 are transmitted into the observation area 20 for providing a background illumination. Providing the background illumination also includes dimming the intensity of the emitted first light 34 by means of the electrical brightness control 60 for the first light emission unit 32, and further includes reducing the intensity of the emitted first light 34, using the neutral density filter 54, below the minimum intensity obtainable or reachable by means of the electrical brightness control 60. Background images of the imaging area (regions in which no fluorescence occurs) are picked-up in other color channels of the camera 26 than the color channel in which the fluorescence is detected, based on the background illumination, and these background images can be observed together with the fluorescence on the monitor 30.

Preferably, the background illumination is provided with an intensity in the observation area 20 which amounts to 0.01% to 0.2%, preferably from 0.05% to 0.1% of the output intensity (maximum intensity) of the first light emission unit 32.

For white light observation of the observation area 20, the entire first wavelength spectrum of the first light 34 is transmitted into the observation area 20 without intensity reduction.

What is claimed is:

1. A system for fluorescence diagnosis, comprising
    a light source;
    a camera comprising a first color channel configured to detect fluorescence in an observation area and further color channels configured to pick up background images for orientation and generation of a color contrast between the first channel and the further color channels, in order to enable tissue differentiation in the observation area,
    the light source comprising:
        a first semiconductor-illuminant based light emission unit configured to emit, in a fluorescence mode, first light in a broadband first wavelength spectrum,
        a second semiconductor-illuminant based light emission unit configured to emit second light in a narrowband second wavelength spectrum for excitation of fluorescence,
        a spectral filter for the first light emission unit that is configured to block spectral components of the first wavelength spectrum which are assigned to a color channel of a camera the fluorescence is to be detected with, and to transmit remaining spectral components of the first wavelength spectrum,
        a brightness control for the first light emission unit configured to dim the intensity of the emitted first light, and
        an optical intensity attenuator for the first light emission unit that is configured to reduce the intensity of the emitted first light below the minimum intensity obtainable through the brightness control without the optical intensity attenuator.

2. The system of claim 1, further comprising a control unit for switching the light source between a white-light mode and a fluorescence mode, wherein the control unit is configured, in the fluorescence mode, to reduce the intensity of the first light emitted from the first light emission unit through the brightness control and to introduce the spectral filter and the optical intensity attenuator into an illumination beam path of the first light emission unit.

3. The system of claim 1, wherein the camera is selected from the group comprising a 1-chip-, 2-chip, 3-chip-camera.

4. The system of claim 1, wherein the spectral filter is movable in order to be introducible into an illumination beam path of the first light emission unit and to be removable from the illumination beam path.

5. The system of claim 1, wherein the optical intensity attenuator is movable in order to be introducible into an illumination beam path of the first light emission unit and to be removable from the illumination beam path.

6. The system of claim 1, wherein the spectral filter and the optical intensity attenuator are arranged one behind the other in direction of an illumination beam path of the first light emission unit on a joint filter carrier, wherein the filter carrier comprises an actuator.

7. The system of claim 1, wherein the first light emission unit comprises a white-light light emitting diode.

8. The system of claim 1, wherein the second light emission unit comprises a narrowband light emitting diode or a laser diode.

9. The system of claim 1, wherein the brightness control comprises an electrical or electronic dimming circuit for the first light emission unit.

10. The system of claim 1, wherein the brightness control is configured to reduce the intensity of the first light emitted from the first light emission unit to a value in a range from 2% to 15% of the maximum output intensity of the first light emission unit.

11. The system of claim 1, wherein the optical intensity attenuator is configured to reduce the intensity of the emitted first light that is adjusted through the brightness control, wherein the intensity of the emitted first light is reduced by a factor of 10 to 1000.

12. The system of claim 1, wherein the optical intensity attenuator comprises a neutral density filter.

13. The system of claim 12, wherein the neutral density filter comprises a neutral density in a range of transmissivity from 1 to 4.

14. The system of claim 12, wherein the neutral density filter comprises a neutral density in a range of transmissivity from 1.5 to 3.

15. The system of claim 1, wherein the spectral filter is selected from the group comprising a long pass filter, a band reflection filter, and a short pass filter.

16. A method of fluorescence diagnosis, comprising the steps:
   emitting, in a fluorescence mode, first light in a broadband first wavelength spectrum from a first semiconductor-illuminant based light emission unit,
   emitting second light in a narrowband second wavelength spectrum from a second semiconductor-illuminant based light emission unit for excitation of fluorescence in an observation area,
   detecting the fluorescence in a first color channel of a camera,
   blocking spectral components of the first wavelength spectrum through a spectral filter, which spectral components are assigned to the first color channel of the camera, and transmitting the remaining spectral components of the first wavelength spectrum to the observation area for providing a background illumination in the fluorescence mode,
   wherein providing the background illumination further comprises:
   dimming the intensity of the emitted first light through a brightness control for the first light emission unit,
   reducing the intensity of the emitted first light below the minimum intensity obtainable through the brightness control, through an optical intensity attenuator
   picking up background images of the observation area in other color channels of the camera than the first color channel, based on the background illumination.

17. The method of claim 16, wherein the background illumination is provided with an intensity in the observation area, that amounts to from 0.01% to 0.2% of the maximum output intensity of the first light emission unit.

18. The method of claim 16, wherein the background illumination is provided with an intensity in the observation area, that amounts to from 0.05% to 0.1% of the maximum output intensity of the first light emission unit.

19. The method of claim 16, wherein the entire first wavelength spectrum of the first light is transmitted into the observation area for a white-light observation of the observation area.

* * * * *